(12) United States Patent
Micinski et al.

(10) Patent No.: US 9,073,959 B2
(45) Date of Patent: *Jul. 7, 2015

(54) PROCESS FOR THE PRODUCTION OF SUCROSE-6-ESTER

(75) Inventors: Edward Micinski, Martinez, GA (US); David Coleman, Daphne, AL (US)

(73) Assignee: TATE & LYLE TECHNOLOGY LIMITED, London (GB)

(*) Notice: Subject to any disclaimer, the term of this patent is extended or adjusted under 35 U.S.C. 154(b) by 466 days.

This patent is subject to a terminal disclaimer.

(21) Appl. No.: 12/901,820

(22) Filed: Oct. 11, 2010

(65) Prior Publication Data

US 2011/0087019 A1  Apr. 14, 2011

Related U.S. Application Data

(60) Provisional application No. 61/250,688, filed on Oct. 12, 2009.

(51) Int. Cl.
| | |
|---|---|
| *C07H 13/04* | (2006.01) |
| *C07H 13/06* | (2006.01) |
| *C07H 13/08* | (2006.01) |
| *C07F 7/22* | (2006.01) |

(52) U.S. Cl.
CPC ............. *C07H 13/04* (2013.01); *C07H 13/08* (2013.01); *C07F 7/2244* (2013.01); *C07F 7/2256* (2013.01); *C07F 7/2232* (2013.01); *C07H 13/06* (2013.01)

(58) Field of Classification Search
CPC ........ C07H 13/04; C07H 13/06; C07H 13/08; C07F 7/2232; C07F 7/2244; C07F 7/2256
See application file for complete search history.

(56) References Cited

U.S. PATENT DOCUMENTS

| | | | |
|---|---|---|---|
| 4,362,869 A | 12/1982 | Jenner et al. |
| 4,380,476 A | 4/1983 | Mufti et al. |
| 4,405,654 A | 9/1983 | Lee |
| 4,783,526 A | 11/1988 | O'Brien et al. |
| 4,826,962 A | 5/1989 | Rathbone et al. |
| 4,889,928 A | 12/1989 | Simpson |
| 4,950,746 A | 8/1990 | Navia |
| 4,980,463 A | 12/1990 | Walkup et al. |
| 5,023,329 A | 6/1991 | Neiditch et al. |
| 5,034,551 A | 7/1991 | Vernon et al. |
| 5,089,608 A | 2/1992 | Walkup et al. |
| 5,128,248 A | 7/1992 | Dordick et al. |
| 5,141,860 A | 8/1992 | Bornemann et al. |
| 5,270,071 A | 12/1993 | Sharp et al. |
| 5,272,137 A | 12/1993 | Blase et al. |
| 5,298,611 A | 3/1994 | Navia et al. |
| 5,354,902 A | 10/1994 | Merciadez et al. |
| 5,374,659 A | 12/1994 | Gowan |
| 5,384,311 A | 1/1995 | Antenucci et al. |
| 5,397,588 A | 3/1995 | Antenucci et al. |
| 5,409,907 A | 4/1995 | Blase et al. |
| 5,440,026 A | 8/1995 | Kahn et al. |
| 5,470,969 A | 11/1995 | Sankey et al. |
| 5,498,709 A | 3/1996 | Navia et al. |
| 5,530,106 A | 6/1996 | Navia et al. |
| 5,593,696 A | 1/1997 | McNally et al. |
| 5,621,005 A | 4/1997 | Gowan |
| 5,658,919 A | 8/1997 | Ratnaraj et al. |
| 5,674,522 A | 10/1997 | Shah et al. |
| 5,817,340 A | 10/1998 | Roche et al. |
| 5,876,759 A | 3/1999 | Gowan |
| 5,898,070 A | 4/1999 | Schulz et al. |
| 5,977,349 A | 11/1999 | Catani et al. |
| 6,080,481 A | 6/2000 | Ochs et al. |
| 6,090,401 A | 7/2000 | Gowan et al. |
| 6,211,246 B1 | 4/2001 | Gelotte et al. |
| 6,258,381 B1 | 7/2001 | Luber et al. |
| 6,265,012 B1 | 7/2001 | Shamil |
| 6,277,409 B1 | 8/2001 | Luber et al. |
| 6,573,400 B1 | 6/2003 | Böttcher et al. |

(Continued)

FOREIGN PATENT DOCUMENTS

| | | |
|---|---|---|
| EP | 0043649 A1 | 1/1982 |
| EP | 0409549 A2 | 1/1991 |

(Continued)

OTHER PUBLICATIONS

Leenheer et al., Anal. Chem., 1987, 59, 1313-1319.*
Pfaudler, wiped film evaporator-WFE, retrived from Internet <<http://www.pesllconline.com/wp-content/uploads/2012/03/Wiped-Film-Evaporator-WFE.pdf>> on Oct. 12, 2012, published in 1997, 12 pages.*
"Pope Brand Wiped-Film Stills Introduced," Published Jul. 27, 2007, Available from http://www.processingtalk.com/news/lat/lat122.html.

(Continued)

*Primary Examiner* — Eric Olson
(74) *Attorney, Agent, or Firm* — RatnerPrestia

(57) ABSTRACT

A process for the production of sucrose-6-ester is disclosed. The process includes, in order, the steps of:

(a) providing a first reaction mixture including sucrose, a reaction vehicle, and an organotin-based acylation promoter;

(b) removing water from the first reaction mixture to afford a second reaction mixture that is substantially free from water; and (c) adding a carboxylic acid anhydride to the second reaction mixture to afford a third reaction mixture, thereby producing a sucrose-6-ester;

wherein:

during step (b), the removing of water includes distillation of water with the reaction vehicle using an apparatus supplying a heat flux of from 500 to 25,000 BTU/hrft$^2$ (1577 to 78865 W/m$^2$) selected from the group consisting of wiped film evaporators, agitated thin film evaporators, falling film evaporators and rising film evaporators.

22 Claims, 1 Drawing Sheet

(56) References Cited

U.S. PATENT DOCUMENTS

| | | |
|---|---|---|
| 6,646,121 B2 | 11/2003 | El Kabbani |
| 6,809,198 B2 | 10/2004 | El Kabbani |
| 6,890,581 B2 | 5/2005 | Vernon et al. |
| 6,939,962 B2 | 9/2005 | Clark et al. |
| 6,943,248 B2 | 9/2005 | Catani et al. |
| 6,998,144 B2 | 2/2006 | Merkel et al. |
| 6,998,480 B2 | 2/2006 | Catani et al. |
| 7,049,435 B2 | 5/2006 | Catani et al. |
| 2002/0131991 A1 | 9/2002 | Milstein et al. |
| 2004/0030124 A1 | 2/2004 | Catani et al. |
| 2006/0188629 A1 | 8/2006 | Liesen et al. |
| 2006/0205936 A1 | 9/2006 | Jia et al. |
| 2006/0276639 A1 | 12/2006 | Fry |
| 2007/0015916 A1 | 1/2007 | El Kabbani et al. |
| 2007/0100139 A1 | 5/2007 | Fry |
| 2007/0160732 A1 | 7/2007 | Deshpande et al. |
| 2007/0227897 A1 | 10/2007 | Li et al. |
| 2007/0270583 A1 | 11/2007 | Ratnam et al. |
| 2009/0076261 A1* | 3/2009 | Xu .............................. 536/127 |

FOREIGN PATENT DOCUMENTS

| | | |
|---|---|---|
| EP | 0475619 A1 | 3/1992 |
| EP | 0708110 A2 | 4/1996 |
| EP | 0 776 903 A1 | 6/1997 |
| WO | 0210180 A1 | 2/2002 |
| WO | WO 03/076453 A1 | 9/2003 |
| WO | WO 03/076454 A1 | 9/2003 |
| WO | WO 2005/090374 A1 | 9/2005 |
| WO | WO 2005/090376 A1 | 9/2005 |
| WO | WO 2006/061855 A2 | 6/2006 |
| WO | WO 2006/120697 A2 | 11/2006 |
| WO | WO 2006/130169 A1 | 12/2006 |
| WO | WO 2007/017899 A2 | 2/2007 |
| WO | WO 2007/023505 A2 | 3/2007 |
| WO | WO 2007/052304 A2 | 5/2007 |
| WO | WO 2008/084197 A1 | 7/2008 |
| WO | WO 2009/035503 A1 | 3/2009 |

OTHER PUBLICATIONS

Osipow et al., "Sugar Esters," *The Journal of the American Oil Chemists' Society*, 1957, 34(4):185-188.

Laughton, Peter, Combined Search and Examination Report under Sections 17 and 18(3), Mar. 17, 2010, 7 pgs.

Nikolai, Joachim, "International Search Report and Written Opinion," Feb. 1, 2011, 10 pgs.

Translation of Japanese Office Action mailed Aug. 26, 2014 in Japanese Application No. 2012-532660.

Jas et al., Chem. Eur. J., 2003, 9, 5708-5723.

Translation of Japanese Office Action mailed Jul. 29, 2014 in counterpart Japanese Application No. 2012-532659.

* cited by examiner

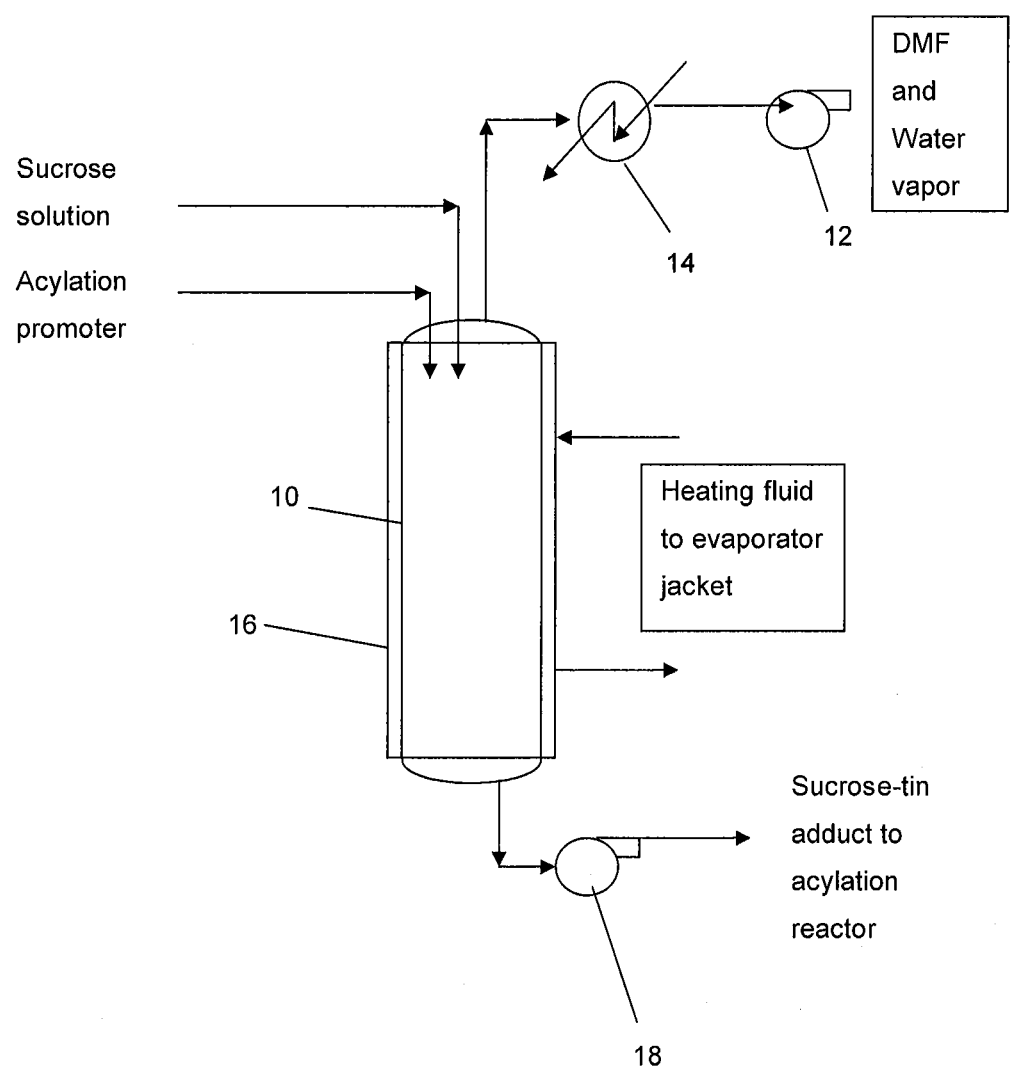

PROCESS FOR THE PRODUCTION OF SUCROSE-6-ESTER

CROSS-REFERENCE TO RELATED APPLICATIONS

This application claims priority of U.S. Provisional patent application No. 61/250,688, filed Oct. 12, 2009, the entirety of which is incorporated herein by reference.

FIELD OF THE INVENTION

This invention relates to sucrose-6-esters and to methods for their preparation.

BACKGROUND OF THE INVENTION

Sucralose (4,1',6'-trichloro-4,1',6'-trideoxygalactosucrose), a high-intensity sweetener that can be used in many food and beverage applications, is a galacto-sucrose having the following molecular structure:

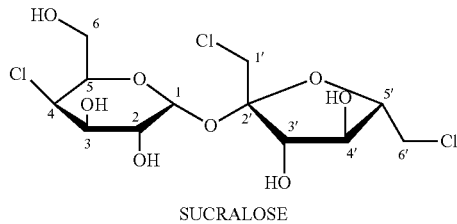

SUCRALOSE

Sucralose is made from sucrose by converting the hydroxyls in the 4, 1' and 6' positions to chloro groups. In this process, the stereochemical configuration at the 4 position is inverted.

In one process for making sucralose from sucrose, sucrose is first converted to a sucrose-6-ester, such as sucrose-6-acetate or sucrose-6-benzoate. The sucrose-6-ester is chlorinated by reaction with a chlorination agent and a tertiary amide, and the resulting reaction mixture heated and then quenched with aqueous alkali. The resulting 4,1',6'-trichloro-4,1',6'-trideoxygalactosucrose ester (sucralose-6-ester) is converted to sucralose, which is subsequently purified and isolated.

Sankey, U.S. Pat. No. 5,470,969; Vernon, EP 0 475 619; Clark, U.S. Pat. No. 6,939,962; and White, EP 0 776 903, the disclosures of which are all incorporated herein by reference, disclose processes for the synthesis of a sucrose-6-ester. The process disclosed by Clark comprises: (a) reacting sucrose in a polar aprotic solvent, such as N,N-dimethyl formamide, with an organotin-based acylation promoter, while continuously adding a non-polar co-solvent capable of removing water by co-distillation, and removing water by co-distillation, to afford a reaction mixture which is substantially free from water, followed by (b) adding a carboxylic anhydride to the reaction mixture and maintaining the resulting reaction mixture at a temperature and for a period of time sufficient to produce a sucrose-6-ester. The non-polar co-solvent is typically a hydrocarbon, such as cyclohexane, n-heptane, toluene, or isooctane.

This process requires large amounts of the non-polar co-solvent, which must be dried before addition and then recovered and re-dried for reuse. Step (a) operates in a temperature region in which decomposition of carbohydrates may occur—even with relatively short reaction times of 20-30 minutes. Because the non-polar co-solvent can cause precipitation of sucrose, the maximum sucrose concentration that can be used in the process is limited by the presence of the non-polar co-solvent. In addition, unreacted sucrose remaining in the sucrose-6-ester product can produce undesirable and difficult to remove tetra-chlorinated species in the subsequent chlorination step. Therefore, a need exists for a process for forming a sucrose-6-ester from sucrose that does not have these disadvantages.

Micinski, PCT Patent Application Publication No. WO2008/084197, discloses a process for the synthesis of a sucrose-6-ester comprising: (a) forming a first reaction mixture comprising sucrose, a polar aprotic solvent, such as N,N-dimethyl formamide, and an organotin-based acylation promoter; (b) removal of water from said first reaction mixture by contacting, in a continuous counter-current manner, with gas or solvent vapour capable of removing water at a temperature, pressure and residence time sufficient to afford a second reaction mixture which is substantially free from water; followed by (c) adding a carboxylic anhydride to said second reaction mixture to afford a third reaction mixture, and maintaining said third reaction mixture at a temperature and for a period of time sufficient to produce a sucrose-6-ester.

This process requires the use of a gas or solvent vapour capable of removing water. According to the present invention, it has been unexpectedly found that use of a gas or solvent vapour capable of removing water is not necessary, and a simpler process has been achieved.

SUMMARY OF THE INVENTION

The invention is a process for producing a sucrose-6-ester. In one aspect the invention is a process comprising, in order, the steps of:

(a) providing a first reaction mixture comprising sucrose, a reaction vehicle, and an organotin-based acylation promoter;
(b) removing water from the first reaction mixture to afford a second reaction mixture that is substantially free from water; and
(c) adding a carboxylic acid anhydride to the second reaction mixture to afford a third reaction mixture, thereby producing a sucrose-6-ester;
in which:
during step (b), the removing of water includes distillation of water with the reaction vehicle using an apparatus supplying a heat flux of from 1577 to 78865 W/m² (500 to 25,000 BTU/hrft²) selected from the group consisting of wiped film evaporators, agitated thin film evaporators, falling film evaporators and rising film evaporators.

In a preferred embodiment, the reaction vehicle is a polar aprotic solvent. Preferably, the polar aprotic solvent is N,N-dimethyl formamide.

In a preferred embodiment, a non-polar co-solvent is not added during step (b).

In a preferred embodiment, the temperature does not exceed about 100° C. in step (b), more preferably does not exceed about 80° C., and more preferably does not exceed about 70° C. In a preferred embodiment, the temperature in step (b) is from about 50° C. to about 75° C.

In a preferred embodiment, the first reaction mixture and/or the second reaction mixture consist essentially of sucrose, polar aprotic solvent, the organotin-based acylation promoter, and/or their reaction products.

In a preferred embodiment, the temperature during step (c) is maintained at 10° C. or less for a period of time sufficient to produce the sucrose-6-ester.

In a preferred embodiment, the organotin-based acylation promoter is a 1,3-di(acyloxy)-1,1,3,3-tetra-(hydrocarbyl)distannoxane or a 1-(acyloxy)-3-hydroxy-1,1,3,3-tetra-(hydrocarbyl)distannoxane. Preferably, the organotin-based acylation promoter is 1,3-diacetoxy-1,1,3,3-tetrabutyldistannoxane or 1-acetoxy-3-hydroxy-1,1,3,3-tetrabutyldistannoxane.

In a preferred embodiment, the carboxylic acid anhydride is acetic anhydride and the sucrose-6-ester is sucrose-6-acetate. In another preferred embodiment, the carboxylic acid anhydride is benzoic anhydride and the sucrose-6-ester is sucrose-6-benzoate.

In a preferred embodiment, the apparatus supplies a heat flux of from 3155 to 63092 $W/m^2$ (1000 to 20000 $BTU/hrft^2$). In another preferred embodiment, the apparatus supplies a heat flux of from 3155 to 47319 $W/m^2$ (1000 to 15000 $BTU/hrft^2$).

In another preferred embodiment, the apparatus supplies a heat flux of from 15773 to 37855 $W/m^2$ (5000 to 12000 $BTU/hrft^2$).

In a preferred embodiment, the apparatus is a film-type evaporator. In a preferred embodiment, the apparatus is an agitated thin film evaporator or a wiped film evaporator.

In a preferred embodiment, the mean temperature difference ($\Delta T$) between the temperature of the heating surface of the apparatus and the temperature of the reaction mixture in step (b) is less than 50° C., preferably less than 30° C., and most preferably is from about 20° C. to about 30° C.

In a preferred embodiment, the distillation is conducted under reduced pressure, i.e. at a pressure below atmospheric pressure. Preferably, the pressure is from 2.7 to 5.3 kPa (20 to 40 mmHg).

In a preferred embodiment, the flow rate in the distillation is from 49 to 732 $kg/hr/m^2$ (10 to 150 $lb/hr/ft^2$). In another preferred embodiment, the flow rate in the distillation is from 244 to 537 $kg/hr/m^2$ (50 to 110 $lb/hr/ft^2$).

In a preferred embodiment, the process additionally comprises, after step (c), the additional step or steps of converting the sucrose-6-ester to sucralose.

Wiped film evaporators, agitated thin film evaporators, falling film evaporators and rising film evaporators are known, and are conventionally used to remove solvent, for example during product isolation after a chemical reaction has taken place. An example of such use of an agitated thin film evaporator in the context of sucralose production can be found in WO 2005/090376 and WO 2005/090374. These apparatus are not conventionally used for carrying out chemical reactions.

It has now surprisingly been found that the above apparatus supplying a heat flux of from 1577 to 78865 $W/m^2$ (500 to 25,000 $BTU/hrft^2$) can be used to remove water from a first reaction mixture comprising sucrose, a reaction vehicle and an organotin-based acylation promoter to afford a second reaction mixture that is substantially free from water. In other words, the above apparatus can be used to carry out a chemical reaction between sucrose and an organotin-based acylation promoter to form a sucrose-tin adduct.

The high heat flux supplied by the apparatus used in step (b) enables water formed by the reaction of sucrose with the organotin-based acylation promoter to be removed quickly and efficiently. This quick and efficient removal of water forces the equilibrium between the first and second reaction mixtures in the direction of the second reaction mixture, and thereby provides short reaction times. Thus, the reaction time for forming the second reaction mixture according to the present invention may be less than 30 minutes or less than 20 minutes, for example less than 10 minutes, or less than 5 minutes. According to some embodiments, the reaction time may be less than 1 minute.

Since the reaction times according to the present invention are short, the reaction will usually be substantially complete after the reaction mixture has passed through the apparatus used in step (b) only once, i.e. after a single pass through the apparatus. In other words, it is not generally necessary to cycle the reaction mixture through the apparatus multiple times. Thus, according to a preferred embodiment of the present invention, the reaction mixture passes through the apparatus only once, i.e. the output from the apparatus is not recycled back to the apparatus, or to another similar apparatus, but progresses directly to step (c).

In the present invention, the high heat flux is preferably advantageously combined with a high flow rate, so that a high heat-flux and a high flow rate are used in the distillation. Thus, the apparatus used in the present invention is an apparatus supplying a heat flux of from 1577 to 78865 $W/m^2$ (500 to 25,000 $BTU/hrft^2$) selected from a wiped film evaporator, an agitated thin film evaporator, a falling film evaporator, a rising film evaporator and the like and preferably handling a flow rate of from 49 to 732 $kg/hr/m^2$ (10 to 150 $lb/hr/ft^2$). The "flow rate" is the amount of material supplied per unit area of the heating surface of the evaporator per unit time.

By virtue of employing a high flow rate in combination with high heat flux, the residence time of the reaction mixture in the apparatus can be kept very low. The apparatus used in the present invention is preferably capable of delivering a high flow rate (e.g. from 49 to 732 $kg/hr/m^2$ (10 to 150 $lb/hr/ft^2$), or from 244 to 537 $kg/hr/m^2$ (50 to 110 $lb/hr/ft^2$)) as well as a high heat flux. This means that the exposure time of the reaction mixture to the distillation conditions can be kept very low, so that any decomposition that the reagents or products may be susceptible to under the distillation conditions (in particular carbohydrate decomposition) is minimised. Thus, the residence time of the reaction mixture within the apparatus used in step (b) may be less than 30 minutes or less than 20 minutes, for example less than 10 minutes, or less than 5 minutes. According to some embodiments, the residence time may be less than 1 minute. This low residence time increases product yields and reduces the level of impurities in the product stream.

The present invention also allows the water of reaction to be removed at a lower temperature than in previous processes. This also results in the amount of carbohydrate decomposition being drastically reduced, even when extended reaction times are used. However, because the reaction proceeds efficiently, even at reduced temperatures, extended reaction times are not necessary.

The present invention also allows the water of reaction to be removed at reduced pressure. The use of a reduced pressure when conducting the distillation in step (b) enables yet further reductions in temperature and/or residence time to be made with consequential further minimisation of carbohydrate decomposition and reaction times.

As will be readily appreciated by the skilled person, the temperature, pressure and flow rate (and thus residence time, which is determined by the flow rate) in step (b) are all interrelated parameters, and should therefore be considered together. For example, reducing the pressure at which the distillation is conducted lowers the temperature of the distillation. Similarly, higher temperatures could be used in conjunction with higher flow rates (i.e. lower residence times). It is a key advantage of the present invention that these parameters can all be adjusted as desired to optimise the process, both chemically and commercially. Prior art processes do not provide such high levels of process flexibility.

The choice of reaction vehicle also affects the above parameters, since water is distilled with the reaction vehicle in step (b). The term "reaction vehicle" means the diluent or solvent in which the process is carried out. The term is meant to indicate that the vehicle may not fully dissolve all of the components of the reaction mixtures at all stages of the process. The reaction vehicle should be stable under the process conditions. The reaction vehicle may include mixtures, for example of a polar aprotic solvent and a non-polar co-solvent, but is preferably a single substance.

The choice of reaction vehicle is determined primarily by the solubility in the reaction vehicle of sucrose, the organotin-based acylation promoter, and the resulting stannylated sucrose product, as well as by safety and toxicity considerations. Preferably the boiling point of the reaction vehicle is greater than the boiling point of water at atmospheric pressure. More preferably, the boiling point of the reaction vehicle is at least 50° C. greater than the boiling point of water at atmospheric pressure. However, if the reaction vehicle forms a low-boiling azeotrope with water, then this boiling point preference is not applicable.

Particularly suitable reaction vehicles for use in the present invention are polar aprotic solvents. Suitable polar aprotic solvents are, for example, tertiary amides such as N-methyl-2-pyrrolidone, N,N-dimethyl acetamide, N,N-diethyl formamide, N,N-diethyl acetamide and, preferably, N,N-dimethyl formamide. Other suitable polar aprotic solvents include dimethyl sulfoxide and hexamethylphosphoramide.

The reaction vehicle may comprise, or consist essentially of, or consist of, polar aprotic solvent(s). The reaction vehicle may also include non-polar co-solvent (see below), but it preferably does not.

Further advantages of the present invention include the fact that the formation of the second reaction mixture proceeds with excellent selectivity for the 6-position, with resulting high selectivity for producing sucrose-6-ester in step (c). Yet a further advantage is that the process can be operated to produce very low levels of unreacted sucrose. As is disclosed in EP-0 776 903-A, residual sucrose is particularly undesirable, because it directly affects the yield of the sucrose-6-ester, and, after chlorination, forms undesirable chlorinated compounds (in particular tetrachlorosucroses) which are difficult to separate from the sucralose-6-ester and sucralose during subsequent processing. Yet another advantage of the present invention lies in the fact that the product stream is a clear, very slightly yellow product, compared with the darker material produced by other processes.

When step (b) is performed in accordance with the present invention, the use of a non-polar co-solvent is not necessary to remove water, and so the addition of the non-polar co-solvent to remove water can, in some embodiments, be completely eliminated. Accordingly, in a preferred embodiment, a non-polar co-solvent is not added during step (b). In another preferred embodiment, the reaction vehicle does not include a non-polar co-solvent, or includes less than 0.3 parts by weight, less than 0.2 parts by weight, less than 0.15 parts by weight, or less than 0.1 parts by weight of non-polar co-solvent.

Not adding non-polar co-solvent in step (b) and/or using a reaction vehicle that does not include non-polar co-solvent or that includes less than 0.3, less than 0.2, less than 0.15, or less than 0.1 parts by weight of non-polar co-solvent simplifies the process, because it is not then necessary to recover and dry large amounts of non-polar co-solvent for reuse. A further advantage is that lower pressures can be used when a non-polar co-solvent is not added, or is present in only small amounts, with resulting lower distillation temperatures and thus reduced decomposition, particularly of carbohydrates. Furthermore, because the process operates at higher concentrations and uses different methods for water removal than previous processes, less energy is used to heat the reaction mixture, which produces a saving in energy cost. In addition, at lower temperatures the reaction has higher selectivity with almost no decomposition, which increases the overall yield of the sucralose preparation process. The process is also more economical to operate because higher concentrations of sucrose can be used, the possibility of sucrose precipitation during the process is reduced, and smaller and consequently less expensive equipment can be used to carry out the process.

Notwithstanding the above, in some embodiments a non-polar co-solvent may be used, for example to aid the removal of water. In these embodiments, it is necessary to accept the consequential solubility limitations, particularly with respect to sucrose, and the issues of recovery of the non-polar co-solvent just discussed, as well as the limits that a non polar co-solvent imposes on the distillation pressure and, therefore, temperature.

Furthermore, use of a gas or solvent vapour capable of removing water is not necessary, resulting in a simpler process. Thus, according to the present invention, the mixture in step (b) is preferably not contacted with a gas or solvent vapour capable of removing water. In particular, the mixture in step (b) is preferably not contacted in a continuous counter-current manner with a gas or solvent vapour capable of removing water.

BRIEF DESCRIPTION OF THE DRAWINGS

FIG. 1 is a flow diagram showing a process according to an embodiment of the present invention.

DETAILED DESCRIPTION OF THE INVENTION

Unless the context indicates otherwise, in the specification and claims, the terms organotin-based acylation promoter, reaction vehicle, polar aprotic solvent, carboxylic acid anhydride, non-polar co-solvent, and similar terms also include mixtures of such materials. Unless otherwise specified, all percentages are percentages by weight and all temperatures are in degrees Centigrade (degrees Celsius). Reduced pressure refers to a pressure less than atmospheric pressure. Temperature refers to the temperature of the relevant reaction mixture, that is, the internal temperature of the liquid phase. (For the avoidance of doubt, it does not refer to the temperature of a heat source, which will, in general, be higher than the internal temperature of the reaction mixture being heated, or of a cooling source, which will, in general, be lower than the internal temperature of the reaction mixture being cooled). Reduced temperature refers to a temperature that is less than the boiling point of the particular reaction vehicle, for example polar aprotic solvent, present in the reaction mixture at atmospheric pressure.

A process for the preparation of sucralose from sucrose involves the following steps. First, the reactive hydroxyl in the 6-position of sucrose is blocked with an ester group, such as acetate or benzoate. The hydroxyls in the 4, 1' and 6'-positions of the resulting sucrose 6-ester are converted to chloro groups, with inversion of the stereochemical configuration at the 4-position. Then the ester group in the 6-position of the resulting sucralose-6-ester is removed, and sucralose, the resulting product, purified and isolated.

Preparation of Sucrose-6-Ester

Selective protection of the 6-hydroxyl of sucrose can be carried out by reaction of sucrose with a carboxylic acid anhydride, such as acetic anhydride or benzoic anhydride, in a reaction vehicle in the presence of an organotin-based acylation promoter, under the reaction conditions described herein, at a temperature and for a period of time sufficient to produce the sucrose-6-ester. The 6-ester group shields the hydroxyl on the 6 position from the chlorination reaction. Accordingly, any ester group that is stable to the conditions of the chlorination reaction and which can be removed under conditions that do not affect the resulting sucralose can be used. When sucrose-6-acetate is prepared, 1,3-diacetoxy-1,1,3,3-tetrabutyldistannoxane, for example, can be used as the organotin-based acylation promoter and acetic anhydride as the carboxylic acid anhydride. Preparation of sucrose-6-esters is disclosed in, for example, O'Brien, U.S. Pat. No. 4,783,526; Navia, U.S. Pat. No. 4,950,746; Simpson, U.S. Pat. No. 4,889,928; Neiditch, U.S. Pat. No. 5,023,329; Walkup, U.S. Pat. No. 5,089,608; Vernon, U.S. Pat. No. 5,034,551; Sankey, U.S. Pat. No. 5,470,969; Kahn, U.S. Pat. No. 5,440,026; Clark, U.S. Pat. No. 6,939,962, and Li, U.S. Pat. Pub. 2007/0227897 A1; the disclosures of which are all incorporated herein by reference.

A typical preparation of sucrose-6-ester employs a two-step process. First, sucrose is contacted in a reaction vehicle with an organotin-based acylation promoter and water of reaction is removed to form a tin-sucrose adduct. Then, the reaction mixture containing the tin-sucrose adduct is contacted with a carboxylic acid anhydride. The sucrose-6-ester can be isolated from the resulting reaction mixture. Alternatively, the organotin acylation promoter and/or its reaction products can be removed from the reaction mixture, and the resulting solution of the sucrose-6-ester in the reaction vehicle used in the next step, conversion of the hydroxyls at the 4, 1', and 6'-positions to chloro groups.

As used herein, the term "reaction vehicle" means the diluent or solvent in which the process is carried out. The term is meant to indicate that the vehicle may not fully dissolve all of the components of the reaction mixtures at all stages of the process. The reaction vehicle should be stable under the process conditions. The reaction vehicle may include mixtures, for example of a polar aprotic solvent and a non-polar co-solvent, but is preferably a single substance.

The choice of reaction vehicle is determined primarily by the solubility in the reaction vehicle of sucrose, the organotin-based acylation promoter, and the resulting stannylated sucrose product, as well as by safety and toxicity considerations. Preferably the boiling point of the reaction vehicle is greater than the boiling point of water at atmospheric pressure. More preferably, the boiling point of the reaction vehicle is at least 50° C. greater than the boiling point of water at atmospheric pressure. However, if the reaction vehicle forms a low-boiling azeotrope with water, then this boiling point preference is not applicable.

Particularly suitable reaction vehicles for use in the present invention are polar aprotic solvents. Suitable polar aprotic solvents are, for example, tertiary amides such as N-methyl-2-pyrrolidone, N,N-dimethyl acetamide, N,N-diethyl formamide, N,N-diethyl acetamide and, preferably, N,N-dimethyl formamide. Other suitable polar aprotic solvents include dimethyl sulfoxide and hexamethylphosphoramide.

The reaction vehicle may comprise, or consist essentially of, or consist of, polar aprotic solvent(s). The reaction vehicle may also include non-polar co-solvent (see below), but it preferably does not.

The amount of the reaction vehicle to be used will also be determined chiefly by the above-mentioned solubility considerations. In general terms, in the case of the preferred embodiments of the present invention where no non-polar co-solvent is added in step (b) and/or where the reaction vehicle consists essentially of polar aprotic solvent(s), it should be noted that the amount of polar aprotic solvent required according to the present invention can typically be less than for prior art systems in which a non-polar co-solvent is added. This is because the solubility of the reaction components in the solvent system is reduced by the presence of a non-polar co-solvent, so that a greater amount of polar aprotic solvent is then required to retain the reaction components in solution. Accordingly, when no non-polar co-solvent is present in accordance with the present invention, a lesser amount of polar aprotic solvent can be used. This provides advantages in terms of the downstream processing of the reaction mixture, as well as economic and environmental advantages. When the polar aprotic solvent is N,N-dimethyl formamide, typically about 4 g to about 22 g of polar aprotic solvent per 1 g of sucrose, preferably about 7 g to about 16 g of polar aprotic solvent per 1 g of sucrose, can be used in the first reaction mixture.

The organotin-based acylation promoter can be any of those known in the art, for example, any of those disclosed in Navia, U.S. Pat. No. 4,950,746; Neiditch, U.S. Pat. No. 5,023,329; Walkup, U.S. Pat. No. 5,089,608; and/or Vernon, EP-0 475 619-A, the disclosures of which are all incorporated herein by reference. In particular, the organotin-based acylation promoter can be: a 1,3-di(hydrocarbyloxy)-1,1,3,3-tetra-(hydrocarbyl)distannoxane; a di(hydrocarbyl)tin oxide; the reaction product of a di(hydrocarbyl)tin oxide and a dihydric alcohol, an alkanolamine, or an enolizable α-hydroxyketone; a 1,3-diacyloxy-1,1,3,3-tetra-(hydrocarbyl)distannoxane; and a 1-acyloxy-3-hydroxy-1,1,3,3-tetra-(hydrocarbyl)distannoxane. An example of the lattermost group of acylation promoters is 1-acetoxy-3-hydroxy-1,1,3,3-tetrabutyldistannoxane. The term "hydrocarbyl" refers to an alkyl, cycloalkyl, aryl, or aralkyl group. The organotin-based acylation promoter is preferably a 1,3-diacyloxy-1,1,3,3-tetra-(hydrocarbyl)distannoxane.

When the organotin-based acylation promoter is a 1,3-di(hydrocarbyloxy)-1,1,3,3-tetra-(hydrocarbyl)distannoxane, the hydrocarbyloxy group is preferably a $C_1$-$C_8$ alkoxy group or phenoxy, more preferably methoxy, ethoxy, n-propyloxy, n-butyloxy, n-pentyloxy or n-hexyloxy, and most preferably a methoxy group. The hydrocarbyl group in turn is preferably an alkyl group, more preferably a $C_1$-$C_8$ alkyl group, and most preferably an n-butyl group.

When the organotin-based acylation promoter is a di(hydrocarbyl)tin oxide, the hydrocarbyl group is preferably an alkyl group, more preferably a $C_1$-$C_8$ alkyl group, and most preferably an n-butyl group.

When the organotin-based acylation promoter is the reaction product of a di(hydrocarbyl)tin oxide and a dihydric alcohol, an alkanolamine, or an enolizable α-hydroxyketone, the di(hydrocarbyl)tin oxide is preferably as described above. The dihydric alcohol can be an alkane diol, preferably having from 2 to 8 carbon atoms. Suitable examples are ethylene glycol, 2,3-propanediol, 2,3-butanediol, 1,3-butanediol, 1,4-butanediol, 1,3-propanediol, 1,2-pentanediol, and 1,2-hexanediol. Alternatively, the dihydric alcohol can be a cycloalkane diol, preferably having from 5 to 8 carbon atoms. Suitable examples are 1,2-cyclohexanediol and 1,2-cyclopentanediol. In each case, the two hydroxyl groups are preferably not more than four carbon atoms distant from each other on the carbon chain to which they are bonded, and preferably they are on adjacent carbon atoms or there is one carbon atom separating the carbon atoms to which the hydroxyl groups are bonded. The alkanolamine is preferably a $C_2$-$C_8$ alkanolamine, and preferably the hydroxyl group and the amino group are not more than four carbon atoms distant from each other on the carbon chain to which they are bonded, and more preferably the hydroxyl group and the amino group are on adjacent carbon atoms or there is only one carbon atom separating the carbon atoms to which the hydroxyl group and the amino group are bonded. Suitable alkanolamines are ethanolamine, 2-amino-1-propanol, and 1-amino-2-propanol. Suitable enolizable α-hydroxyketones are 2-hydroxy-2-phenylacetophenone and 3-hydroxy-2-butanone.

In some embodiments, the organotin-based acylation promoter is a 1,3-diacyloxy-1,1,3,3-tetra-(hydrocarbyl)distannoxane. The hydrocarbyl group of the 1,3-diacyloxy-1,1,3,3-tetra-(hydrocarbyl)distannoxane is preferably an alkyl group, more preferably a $C_1$-$C_8$ alkyl group, and most preferably a butyl group, so that 1,1,3,3-tetrabutyldistannoxanes are particularly preferred. It is convenient if the acyloxy group matches that of the carboxylic anhydride to be used, so that, for example, when a sucrose-6-acetate is being prepared, 1,3-diacetoxy-1,1,3,3-tetrabutyldistannoxane (distannoxane diacetate or DSDA) is most preferred. The above hydrocarbyl and acyloxy groups are also preferred in the case that a 1-acyloxy-3-hydroxy-1,1,3,3-tetra-(hydrocarbyl)distannoxane is used as the organotin-based acylation promoter.

When the organotin-based acylation promoter is a dinuclear species containing two atoms of tin per molecule (e.g. a distannoxane), preferably 0.5 to 2.5 molar equivalents, more preferably 0.75 to 1.2 molar equivalents, still more preferably 0.9 to 1.1 molar equivalents, and most preferably 1.0 molar equivalents of acylation promoter per mole of sucrose is present in the reaction mixture. When the organotin-based acylation promoter is a mononuclear species containing one atom of tin per molecule (e.g. a di(hydrocarbyl)tin oxide), preferably 0.5 to 2.5 molar equivalents, more preferably 0.8 to 1.5 molar equivalents, and most preferably 1.2 molar equivalents of acylation promoter per mole of sucrose is present in the reaction mixture.

In the first step (step (a)), a first reaction mixture comprising sucrose in a reaction vehicle is prepared by dissolving sucrose in the reaction vehicle. The reaction vehicle is preferably a polar aprotic solvent, typically N,N-dimethyl formamide. Slight heating can be used to dissolve the sucrose. Then the organotin-based acylation promoter is added to the reaction mixture. Then, in step (b), water is removed from the first reaction mixture by distillation with the reaction vehicle using an apparatus supplying a heat flux of from 1577 to 78865 W/m² (500 to 25,000 BTU/hrft²) selected from a wiped film evaporator, an agitated thin film evaporator, a falling film evaporator, a rising film evaporator and the like. This distillation removes the water of reaction and drives the reaction to the sucrose-tin adduct in a very efficient manner, thereby affording the second reaction mixture.

By "an apparatus supplying a heat flux of from 1577 to 78865 W/m² (500 to 25,000 BTU/hrft²) selected from a wiped film evaporator, an agitated thin film evaporator, a falling film evaporator, a rising film evaporator and the like" is meant any wiped film evaporator, agitated thin film evaporator, falling film evaporator, or rising film evaporator capable of supplying a heat flux of from 1577 to 78865 W/m² (500 to 25,000 BTU/hrft²), as well as any equivalent evaporation apparatus that is capable of supplying a heat flux of from 1577 to 78865 W/m² (500 to 25,000 BTU/hrft²). In other words, the present invention is not limited to the specific evaporators mentioned, but extends to similar evaporation apparatus capable of supplying a heat flux of from 1577 to 78865 W/m² (500 to 25,000 BTU/hrft²). The evaporation apparatus should also preferably be capable of handling a flow rate of from 49 to 732 kg/hr/m² (10 to 150 lb/hr/ft²), or from 244 to 537 kg/hr/m² (50 to 110 lb/hr/ft²). By "flow rate" is meant the amount of material supplied per unit area of the heating surface of the evaporator per unit time. Controlling the flow rate directly controls the residence time of the reaction mixture in the apparatus: the greater the flow rate, the lower the residence time will be. According to the present invention, the residence time of the reaction mixture within the apparatus used in step (b) may be less than 30 minutes or less than 20 minutes, for example less than 10 minutes, or less than 5 minutes. According to some embodiments, the residence time may be less than 1 minute. Higher flow rates (and thus lower residence times) reduce the level of carbohydrate degradation during the distillation.

In a preferred embodiment, the apparatus is capable of supplying a heat flux of from 3155 to 47319 W/m² (1000 to 15000 BTU/hrft²). In another preferred embodiment, the apparatus is capable of supplying a heat flux of from 15773 to 37855 W/m² (5000 to 12000 BTU/hrft²). In a preferred embodiment, the apparatus is a film-type evaporator.

In the process according to the present invention, an added non-polar co-solvent capable of removing water by co-distillation, such as described in Sankey, U.S. Pat. No. 5,470,969; White, EP 0 776 903; and Vernon, EP 0 475 619, the disclosures of which are incorporated herein by reference, is not necessary for efficient removal of the water of reaction. Consequently, in the current invention, the reaction may be carried out with, but is preferably carried out without, addition of such a non-polar co-solvent. Such solvents are typically ones that do not react with the reaction vehicle or components thereof, the organotin-based acylation promoter, or the sucrose; that produce a mixture with the reaction vehicle, the organotin-based acylation promoter, and the sucrose; that reflux with an internal reaction temperature within the range of from about 75° C. to about 153° C., preferably less than 100° C.; that co-distil with water; and that do not render the sucrose insoluble. Such solvents are typically those that are immiscible with water and form a constant-composition minimum-boiling azeotrope with water, such as saturated hydrocarbons, aromatic hydrocarbons, chlorinated hydrocarbons, ketones, and ethers. Examples of such solvents include cyclohexane, n-heptane, toluene, and isooctane (2,2,4-trimethylpentane). Preferably, such non-polar co-solvents are not present at all in the first or second reaction mixtures, or the first and second reaction mixtures at all times comprise less than 30% (w/w) of non-polar co-solvent, less than 20% (w/w) of non-polar co-solvent, less than 15% (w/w) of non-polar co-solvent, or less than 10% (w/w) of non-polar co-solvent. In one further aspect of the invention, the first reaction mixture and the second reaction mixture, formed after removal of water and at least a portion of the reaction vehicle, preferably consist essentially of the sucrose, polar aprotic solvent, the organotin-based acylation promoter, and/or their reaction products.

In the distillation process of step (b), unlike in the process of Micinski, PCT Patent Application Publication no. WO2008/084197, a gas or solvent vapour capable of removing water is preferably not employed, other than the reaction vehicle itself, in particular when the reaction vehicle is, or is predominantly, polar aprotic solvent. Thus, the mixture in step (b) is preferably not contacted with a gas or solvent vapour capable of removing water, other than the reaction vehicle itself, in particular when the reaction vehicle is, or is predominantly, polar aprotic solvent. Examples of the gas used in the process of Micinski are nitrogen, argon, air, helium, and carbon dioxide. Examples of the classes of solvent vapour used in the process of Micinski are saturated hydrocarbons, aromatic hydrocarbons, chlorinated hydrocarbons, ketones, esters, and ethers. Specific examples of the solvent vapour are cyclohexane, n-heptane, isooctane (2,2,4-trimethylpentane), benzene, toluene, diethyl ether, chloroform, carbon tetrachloride, hexane, ethyl acetate, and methyl acetate. Hydrocarbons are preferred, and cyclohexane, n-heptane, toluene, and isooctane (2,2,4-trimethylpentane) are particularly preferred.

In step (b), the distillation is preferably conducted under reduced pressure, that is, a pressure less than atmospheric pressure. Preferably, the pressure is from about 0.07 kPa (0.5 mmHg) to atmospheric pressure, and most preferably the pressure is from about 2.7 to 5.3 kPa (20 to 40 mmHg).

The distillation in step (b) is preferably conducted at a reduced temperature, that is a temperature less than the boiling point of the reaction vehicle at atmospheric pressure. Preferably, the temperature does not exceed about 100° C. in step (b), more preferably does not exceed about 80° C., and more preferably does not exceed about 70° C. In a preferred embodiment, the temperature is between below 80° C. and about 0° C. Preferably the temperature in step (b) does not exceed about 80° C., about 78° C., about 75° C., or about 70° C. In other embodiments, the temperature in step (b) is below 60° C. or below 50° C. Preferably, the temperature in step (b) is maintained between about 80° C. and about 0° C., between about 78° C. and about 5° C., between about 75° C. and about 10° C., or between about 70° C. and about 15° C., during the removing of water. Most preferably, the temperature in step (b) is from about 60° C. to about 80° C.

In a preferred embodiment, the mean temperature difference ($\Delta T$) between the temperature of the heating surface of the apparatus and the temperature of the reaction mixture in step (b) is less than 50° C., preferably less than 30° C., and most preferably is from about 20° C. to about 30° C.

The temperature in step (b) can be controlled by controlling the pressure at which the distillation is conducted. Preferably the distillation of step (b) is conducted at a pressure between about 8.7 kPa (about 65 mmHg) and about 0.07 kPa (about 0.5 mmHg), between about 6.7 kPa (about 50 mmHg) and about 2.0 kPa (about 15 mmHg), or between about 5.3 kPa (about 40 mmHg) and about 2.7 kPa (about 20 mmHg).

By use of the process of the present invention, removal of the water of reaction can be achieved at a significantly lower temperature than previous methods. The lower temperature causes significantly less carbohydrate decomposition, even with extended reaction times. However, because the reaction proceeds efficiently, even at reduced temperatures, extended reaction times are not necessary. Removal of the water of reaction can also be accomplished without an added non-polar co-solvent. The resulting product stream is a clear, very slightly yellow product, compared with the darker material produced by other processes.

As will be apparent to those skilled in the art, the organotin-based acylation promoter can be introduced into the reaction mixture by addition of a solution of the organotin-based acylation promoter in a non-polar aprotic solvent, such as one of the non-polar co-solvents capable of removing water by co-distillation discussed above.

For example, the organotin-based acylation promoter can be added to the reaction mixture in cyclohexane solution. Consequently, a small amount (for example less than 30% w/w, less than 20% w/w, less than 15% w/w, or less than 10% w/w with respect to the reaction vehicle) of a non-polar aprotic solvent can be present in the reaction mixture at the beginning of step (a). As will be apparent to the skilled-person, such low levels of non-polar co-solvent are far below the levels required in prior art processes to aid water removal. This small amount of non-polar co-solvent is then removed at the beginning of the distillation. Preferably, no additional non-polar co-solvent is added to the reaction mixture during step (b).

In some embodiments, for example when the organotin-based acylation promoter is added in solid form, it is possible for the reaction mixture at the beginning of step (b) to be in the form of a slurry. The reaction mixture then becomes homogeneous as the reaction proceeds. This applies in particular when the organotin-based acylation promoter is a di(hydrocarbyl)tin oxide, for example dibutyltin oxide (DBTO).

Following removal of the water of reaction during step (b), in the next step (step (c)), the solution of the sucrose-tin adduct produced in step (b) is cooled to near or below room temperature and mixed with a suitable esterifying agent, such as a carboxylic acid anhydride, to produce a third reaction mixture. Preferably, the third reaction mixture is maintained at about 10° C. or less for a period of time sufficient to produce the sucrose-6-ester. The reaction takes place rapidly, even at less than −20° C. If necessary, small amounts of an aprotic co-solvent, for example, a hydrocarbon such as cyclohexane, can be added during step (c) to keep the materials in solution. Any solvent added after step (b) and before and/or during step (c) should be dry so that the carboxylic acid anhydride is not hydrolyzed to its corresponding carboxylic acid.

The carboxylic acid anhydride is preferably added in an amount of from 0.8 to 1.5 molar equivalents (per mole of sucrose starting material), more preferably from 1.05 to 1.35 molar equivalents, still more preferably from 1.1 to 1.25 molar equivalents, and most preferably 1.15 molar equivalents. Too much carboxylic acid anhydride produces excessive amounts of over carboxylation of sucrose (i.e., formation of diesters, triesters, etc.). Too little carboxylic acid anhydride produces unreacted sucrose.

The process can be used to prepare a variety of sucrose-6-esters, provided that the appropriate carboxylic acid anhydride is available. For example, the method can be used to prepare sucrose-6-acetate, by the use of acetic anhydride; sucrose-6-benzoate, by the use of benzoic anhydride; sucrose-6-acrylate, by the use of acrylic anhydride; sucrose-6-methacrylate, by the use of methacrylic anhydride; sucrose-6-propionate by the use of propionic anhydride; sucrose-6-butyrate, by the use of butanoic anhydride; etc.

After sufficient time at a temperature near or below room (i.e., ambient) temperature, the mixture is quenched with water. The course of the reaction can be followed by, for example, high pressure liquid chromatography.

The organotin-based acylation promoter is available for recycle after separation of the sucrose-6-ester. A process for the recovery and re-use of the organotin-based acylation promoter is disclosed in Vernon, U.S. Pat. No. 5,034,551, the disclosure of which is incorporated herein be reference. When the organotin-based acylation promoter is a 1,3-diacyloxy-1,1,3,3-tetra-(hydrocarbyl)distannoxane, it is preferably recovered after step (c) and reused. A small amount of water and, if necessary, a small amount of a non-polar aprotic solvent, typically a hydrocarbon such as cyclohexane, are added to the reaction mixture after step (c). The reaction mixture partitions between water and the non-polar aprotic solvent, creating an upper (i.e., less dense) phase comprising 1,3-diacyloxy-1,1,3,3-tetra-(hydrocarbyl)distannoxane and the non-polar aprotic solvent, and a lower (i.e., more dense) phase comprising the sucrose-6-ester; the polar aprotic solvent, for example, N,N-dimethyl formamide; water; and carboxylic acid. The upper phase is removed, and the lower phase extracted with the non-polar aprotic solvent. The non-polar aprotic solvent extracts are combined and concentrated, preferably under reduced pressure, and treated with an alkoxide. The recovered 1,3-diacyloxy-1,1,3,3-tetra-(hydrocarbyl) distannoxane can be further purified by conventional techniques.

The lower layer contains sucrose-6-ester, carboxylic acid (that was formed by the reaction of carboxylic acid anhydride and sucrose plus any that might have been formed by hydrolysis of excess anhydride with the added water), unreacted sucrose, a small amount of other sucrose esters, and the polar aprotic solvent. Preferably, the carboxylic acid is removed from the solution of sucrose-6-ester in polar aprotic solvent prior to further processing of the sucrose-6-ester. When the acid is relatively volatile such as acetic acid, it can be removed, for example, by fractional distillation under reduced pressure, to remove water, any remaining non-polar aprotic solvent, and carboxylic acid. Make-up polar aprotic solvent can be added during or after the distillation, especially if the resulting mixture containing the sucrose-6-ester is to be further processed in the same solvent, such as in N,N-dimethyl formamide. The sucrose-6-ester in residual polar aprotic solvent may then be used directly in, for example, the chlorination process disclosed in Walkup, U.S. Pat. No. 4,980,463, the disclosure of which is incorporated herein by reference. Optionally, sucrose-6-ester can be recovered by conventional procedures such as crystallization from a solvent such as methanol and used in the chlorination process.

The sucrose-6-ester can be obtained with high selectivity and can be in high yield. When the sucrose-6-ester is sucrose-6-acetate, the selectively of the 6-monoacetate over other acetylated products can be very high, with normalized assays of 6-monoacetate as high as 85-90% relative to total carbohydrates. Unreacted sucrose, which produces undesirable and difficult to remove tetra-chlorinated species in the chlorination step, can be reduced to <0.1%, and, in some embodiments, to undetectable levels (i.e. <0.01%).

One embodiment of a process according to the present invention is shown in FIG. 1. Referring to FIG. 1, a solution containing sucrose (typically about 8-10%) in a polar aprotic solvent, such as N,N-dimethyl formamide, is added to a vessel (10), which is an apparatus supplying a heat flux of from 1577 to 78865 W/m$^2$ (500 to 25,000 BTU/hrft$^2$) selected from a wiped film evaporator, an agitated thin film evaporator, a falling film evaporator, a rising film evaporator and the like. Vessel (10) may include an agitator (not shown). An organotin-based acylation promoter, such as 1,3-diacetoxy-1,1,3,3-tetrabutyldistannoxane (DSDA) is also added.

A vacuum is maintained by a vacuum pump (12). The vapors of the polar aprotic solvent and water are condensed by a condenser (14).

The pressure in vessel (10) is selected so that the temperature of the reaction mixture does not exceed the desired temperature, for example about 80° C. or below. As will be apparent to those skilled in the art, the temperature of the reaction mixture can be adjusted to temperatures less than 80° C. by reducing the pressure in vessel (10). Heat can be added to the vessel (10) by supplying heat to a heating jacket (16) on the vessel (10).

A stream from the bottom of vessel (10) is taken into a reactor where it is cooled and acylated as previously described. The stream can be fed into the acylation reactor by any convenient means, for example by a circulation pump (18).

It is important that the feed to the acylation reaction be extremely dry. If desired, an additional water removal process (not shown) can be used prior to acylation. For example, a small single stage flash unit can be inserted between the vessel (10) and the acylation reactor to remove any small amount of water that may have been introduced into the process.

Conversion of Sucrose-6-Ester to Sucralose-6-Ester

To convert sucrose-6-ester to sucralose-6-ester, the hydroxyls at the 4, 1', and 6' positions of sucrose-6-ester are converted to chloro groups and the stereochemical configuration at the 4 position is inverted. Conversion of the hydroxyls in the 4, 1', and 6' positions of the ester to chloro groups with inversion of the stereochemical configuration at the 4 position is disclosed in Walkup, U.S. Pat. No. 4,980,463; Jai, U.S. Pat. Pub. 2006/0205936 A1; and Fry, U.S. Pat. Pub. 2007/0100139 A1; the disclosures of which are all incorporated herein by reference.

This chlorination process comprises the following steps. A reaction mixture is prepared comprising the sucrose-6-ester, a tertiary amide, and at least seven molar equivalents of a chlorination agent. For example, in one process, the sucrose-6-ester can be added in a feed stream that comprises about 20 wt % to about 40 wt % of the sucrose-6-ester. The ratio by weight of tertiary amide to total carbohydrate in the reaction mixture may be about 5:1 to about 12:1. Alternatively, a preformed chloroformiminium salt, such as (chloromethylene)dimethylammonium chloride (Arnold's reagent), can be used. (Chloromethylene)dimethylammonium chloride can be prepared, for example, by the reaction of phosgene with N,N-dimethyl formamide. Typically, the molar ratio of the (chloromethylene)dimethylammonium salt to the sucrose-6-ester is about 7:1 to about 11:1.

Subsequently, the hydroxyl groups of the sucrose-6-ester at the 2, 3, 4, 1', 3', 4', and 6' positions are converted to O-alkylformiminium groups. The resulting reaction mixture is heated at a temperature or temperatures and for a period of time or times sufficient to produce a product containing a derivative of sucralose-6-ester in which the remaining hydroxyl groups remain as O-alkylformiminium groups. For example, Walkup, U.S. Pat. No. 4,980,463, the disclosure of which is incorporated herein by reference, and Fry, U.S. 2007/0100139, the disclosure of which is incorporated herein by reference, disclose such processes.

Because formation of a chloroformiminium salt or Vilsmeier reagent is not essential to the chlorination reaction, chlorination agent refers to any compound that can be used to form a chloroformiminium salt or Vilsmeier reagent, or that can convert the hydroxyl groups of a sucrose-6-ester to chloro groups. Some chlorination agents that can be reacted with a tertiary amide to form a chloroformiminium salt include, for example, phosgene, phosphorus oxychloride, phosphorus pentachloride, thionyl chloride, sulfuryl chloride, oxalyl chloride, trichloromethyl chloroformate ("diphosgene"), bis (trichloromethyl) carbonate ("triphosgene"), and methane sulfonylchloride. Tertiary amides that can be used include, for example, N,N-dimethyl formamide (DMF), N-formyl piperidine, N-formyl morpholine, and N,N-diethyl formamide. When N,N-dimethyl formamide is used as the tertiary amide, it can also be used as the reaction solvent. Co-solvents can be used at up to about 80 vol % or more of the liquid phase of the reaction medium. Useful co-solvents are those which are both chemically inert and which provide sufficient solvent power to enable the reaction to become essentially homogeneous at the monochlorination stage, for example toluene, o-xylene, 1,1,2-trichloroethane, 1,2-diethoxyethane, and diethylene glycol dimethyl ether.

Quenching of the reaction mixture restores the hydroxyl groups at the 2, 3, 3', and 4' positions and forms the sucralose-6-ester. The reaction mixture can be quenched by the addition of about 0.5 to about 2.0 molar equivalents, typically about 1.0 to about 1.5 molar equivalents, of alkali relative to the amount of chlorination agent used in the reaction. An aqueous solution of an alkali metal hydroxide, such as sodium or potassium hydroxide; an aqueous slurry of an alkaline earth metal hydroxide, such as calcium hydroxide; or aqueous ammonium hydroxide can be used to quench the reaction. For example, an aqueous solution of an alkali metal hydroxide, such as aqueous sodium hydroxide, that contains about 5 wt % to about 35 wt %, typically about 8 wt % to about 20 wt %, and preferably about 10 wt % to about 12 wt % can be used.

As described below, quenching can be carried out by addition of alkali to the reaction mixture, by a dual stream process, or by a circulated process. In each case pH and temperature are controlled during addition of the alkali. Quenching is typically carried out at a pH between about 8.5 to about 10.5 and at a temperature of about 0° C. to about 60° C. Preferably, the pH should not be permitted to rise above about 10.5 during the course of the quenching reaction.

In the dual stream process, quenching is carried out by slow addition of the aqueous alkali with simultaneous slow addition of the chlorination reaction material into a reaction vessel. The chlorination reaction mixture and aqueous alkali are simultaneously added slowly until the desired quantity of chlorination reaction mixture has been added. Further aqueous alkali is added until the desired pH is reached. Then the temperature and pH are maintained at the desired levels for the remainder of the reaction. This process can be a batch or continuous process.

In the circulated process, quenching is carried out by circulating the chlorination reaction mixture from a vessel through a circulation loop. Chlorination reaction mixture and aqueous alkali are added slowly into this circulation loop. Sufficient aqueous alkali is added until the desired pH is reached. Then the temperature and pH are maintained at the desired levels for the remainder of the reaction. This process can be a batch or continuous process.

Following quenching, the reaction mixture can be neutralized by the addition of aqueous acid, for example aqueous hydrochloric acid. The resulting mixture comprises sucralose 6-ester, other carbohydrate including chlorinated carbohydrate impurities, unreacted tertiary amide, and salts in an aqueous solvent in which the predominant solvent is water.

Conversion of Sucralose-6-Ester to Sucralose

The resulting mixture typically comprises both sucralose and sucralose-6-ester. The mixture of sucralose and sucralose-6-ester can be converted to sucralose, and the resulting sucralose purified and isolated by methods known in the art. Methods for hydrolyzing sucralose-6-ester, isolating sucralose, and/or purifying sucralose are disclosed, for example, in Catani, U.S. Pat. Nos. 5,977,349, 6,943,248, 6,998,480, and 7,049,435; Vernon, U.S. Pat. No. 6,890,581; El Kabbani, U.S. Pat. Nos. 6,809,198, and 6,646,121; Navia, U.S. Pat. Nos. 5,298,611 and 5,498,709, and U.S. Pat. Pub. 2004/0030124; Liesen, U.S. Pat. Pub. 2006/0188629 A1; Fry, U.S. Pat. Pub. 2006/0276639 A1; El Kabbani, U.S. Pat. Pub. 2007/0015916 A1; Deshpande, U.S. Pat. Pub. 2007/0160732 A1; and Ratnam, U.S. Pat. Pub. 2007/0270583 A1; the disclosures of which are all incorporated herein by reference.

For example, (a) sucralose-6-ester can be hydrolyzed to sucralose by raising the pH of the reaction mixture to about 11±1 at a temperature and for a time sufficient to effect removal of the protecting group, and (b) the tertiary amide is removed by, for example, steam stripping. Either step (a) or step (b) can be carried out first. Sucralose is recovered from the resulting mixture by batch, continuous, or continuous counter-current extraction of the mixture with an organic solvent, such as dichloromethane, chloroform, 2-butanone, cyclohexanone, ethyl acetate, or a mixture thereof. The organic extract can be decolorized with carbon, concentrated, and seeded with sucralose crystals to precipitate sucralose. The resulting sucralose crystals can be further purified by recrystallization from, for example, water or ethyl acetate. Alternatively, the sucrose can be purified by chromatography. Purifying sucralose by an initial non-crystallization purification procedure, such as solvent extraction or chromatography, followed by three or more sequential crystallization steps from, for example, water or ethyl acetate, and recycle of the mother liquor remaining from each crystallization step to the feed of another crystallization or purification step is also suitable.

Alternatively, conversion of sucralose-6-ester to sucralose can be carried in methanol containing sodium methoxide. A trans-esterification reaction occurs that forms sucralose and the methyl ester of the acid, for example methyl acetate when the sucralose-6-ester is sucralose-6-acetate. The methyl ester of the acid can be removed by distillation.

INDUSTRIAL APPLICABILITY

The process of the invention is useful in the preparation of sucralose. Sucralose is a high-intensity sweetener that can be used in many food and beverage applications, as well as in other applications. Such applications include, for example, beverages, combination sweeteners, consumer products, sweetener products, tablet cores (Luber, U.S. Pat. No. 6,277,409), pharmaceutical compositions (Luber, U.S. Pat. No. 6,258,381; Roche, U.S. Pat. No. 5,817,340; and McNally, U.S. Pat. No. 5,593,696), rapidly absorbed liquid compositions (Gelotte, U.S. Pat. No. 6,211,246), stable foam compositions (Gowan, Jr., U.S. Pat. No. 6,090,401), dental floss (Ochs, U.S. Pat. No. 6,080,481), rapidly disintegrating pharmaceutical dosage forms (Gowan, Jr., U.S. Pat. No. 5,876,759), beverage concentrates for medicinal purposes (Shah, U.S. Pat. No. 5,674,522), aqueous pharmaceutical suspensions (Ratnaraj, U.S. Pat. No. 5,658,919; Gowan, Jr. U.S. Pat. Nos. 5,621,005 and 5,374,659; and Blase, U.S. Pat. Nos. 5,409,907 and 5,272,137), fruit spreads (Antenucci, U.S. Pat. No. 5,397,588; and Sharp, U.S. Pat. No. 5,270,071), liquid concentrate compositions (Antenucci, U.S. Pat. No. 5,384,311), and stabilized sorbic acid solutions (Merciadez, U.S. Pat. No. 5,354,902). The determination of an acceptable sweetness can be accomplished by a variety of standard "taste test" protocols known in the art which are well known to those skilled in the art, such as, for example, the protocols referred to in Merkel, U.S. Pat. No. 6,998,144, and Shamil, U.S. Pat. No. 6,265,012.

The advantageous properties of this invention can be observed by reference to the following examples, which illustrate but do not limit the invention.

EXAMPLES

Glossary

DMF N,N-dimethyl formamide
DSDA 1,3-diacetoxy-1,1,3,3-tetrabutyldistannoxane (distannoxane diacetate); $(C_4H_9)_2Sn(OAc)$—O—$Sn(OAc)(C_4H_9)_2$

Example 1

This example illustrates an embodiment of the present invention in which a Wiped Film Evaporator (WFE) is used in step (b).

The equipment used for this example was a glass Pope Evaporator with a c. 5 cm (2-inch) diameter inner tube c. 20 cm (8 inches) in length. The total available heat transfer surface for this laboratory unit is c. 0.032 m² (0.34 square feet). The laboratory evaporator used in this example was constructed of glass, which limits the maximum attainable heat flux.

The parameters used for this example were as follows:
1. Dilute feed with 77.02 g of sucrose, 902.48 g of DMF, and 144.97 g of DSDA
2. Heating fluid (on jacket of evaporator) at 85° C.
3. Vacuum set at 2.7-4.7 kPa (20-35 mmHg), resulting in an internal reaction temperature of ~72° C.
4. Feed flow rate of 21.2 g/min (15.0% of full scale)
5. Wiper speed of about 150 rpm (35% of full scale)
6. Residence time of approx. 44 sec as measured by "wave front"
7. Heating was adjusted to strip 55-60% of the feed, which equates to a heat flux of ~3470+ W/m² (~1100+ BTU/hrft²).

The WFE was equipped with an overhead condenser and bottoms fraction collector. The system was started up by first applying a vacuum and applying heat to the WFE jacket. The feed was then started using a metering pump. The internal reaction temperature was determined by measuring the temperature of the vapors going to the overhead condenser. After a short period of stabilization, various fractions were taken and acetylated (using acetic anhydride) in a separate apparatus. The results for this run after acetylation are contained in the table below. The time column in the table represents the number of minutes the solution was held in the acetylation reactor after adding acetic anhydride.

| Sample | Time (min) | S6A | S2A | Total other chlorinated sucroses | Unreacted sucrose | Total |
|---|---|---|---|---|---|---|
| A | 30 | 83.84 | 3.26 | 5.19 | 7.72 | 100.00 |
| B | 60 | 86.10 | 3.35 | 6.45 | 4.10 | 100.00 |
| C | 150 | 86.61 | 3.39 | 8.55 | 1.44 | 100.00 |
| D | 195 | 86.22 | 3.39 | 9.36 | 1.04 | 100.00 |

S6A = sucrose-6-acetate; S2A = sucrose-2-acetate

Example 2

This example illustrates an embodiment of the present invention in which a Falling Film Evaporator (FFE) is used in step (b).

The equipment used for this example was a glass Pope Evaporator with a c. 5 cm (2-inch)) diameter inner tube c. 20 cm (8 inches) in length. The Teflon® wiper blades were removed so that the equipment would function as a falling film evaporator. The total available heat transfer surface for this laboratory unit is c. 0.032 m² (0.34 square feet). The laboratory evaporator used in this example was constructed of glass, which limits the maximum attainable heat flux.

The parameters used for this example were as follows:
1. Dilute feed with 77.13 g of sucrose, 900.25 g of DMF, and 144.24 g of DSDA
2. Heating fluid (on jacket of evaporator) at 95° C.
3. Vacuum set at 2.7 to 5.3 kPa (20-40 mmHg), resulting in an internal reaction temperature of ~71° C.
4. Feed flow rate of 21.2 g/min (15.0% of full scale)
5. Residence time of less than 45 sec
6. Heating was adjusted to strip 62-68% of the feed, which equates to a heat flux of ~3943+ W/m² (~1250+ BTU/hrft²).

The FFE was equipped with an overhead condenser and bottoms fraction collector. The system was started up by applying a vacuum and applying heat to the FFE jacket. The feed was then started using a metering pump. The internal reaction temperature was determined by measuring the temperature of the vapors going to the overhead condenser. After a short period of stabilization, various fractions were taken and acetylated (using acetic anhydride) in a separate apparatus. The results for this run after acetylation are contained in the table below. The time column in the table represents the number of minutes the solution was held in the acetylation reactor after adding acetic anhydride.

| Sample | Time (min) | S6A | S2A | Total other chlorinated sucroses | Unreacted Sucrose | Total |
|---|---|---|---|---|---|---|
| A | 30 | 84.72 | 3.08 | 5.26 | 6.95 | 100.00 |
| B | 60 | 86.60 | 3.15 | 7.36 | 2.89 | 100.00 |
| C | 90 | 86.48 | 3.18 | 8.59 | 1.76 | 100.00 |
| D | 120 | 85.86 | 3.19 | 9.82 | 1.14 | 100.00 |
| E | 180 | 84.57 | 3.18 | 11.63 | 0.62 | 100.00 |

S6A = sucrose-6-acetate; S2A = sucrose-2-acetate

Example 3

Example 1 was repeated but heating was adjusted to strip 35% of the DMF, which equates to a heat flux of approximately 3155 W/m² (1000 BTU/hr/ft²). The results for this run after acetylation are contained in the table below. The time column in the table represents the number of minutes the solution was held in the acetylation reactor after adding acetic anhydride.

| Sample | Time (min) | S6A | S2A | Total other chlorinated sucroses | Unreacted Sucrose | Total |
|---|---|---|---|---|---|---|
| A | 30 | 82.89 | 4.20 | 6.93 | 5.98 | 100.00 |
| B | 90 | 82.80 | 4.34 | 12.08 | 0.79 | 100.00 |
| C | 120 | 80.94 | 4.35 | 14.55 | 0.17 | 100.00 |
| D | 240 | 78.35 | 4.32 | 17.33 | 0.00 | 100.00 |

S6A = sucrose-6-acetate; S2A = sucrose-2-acetate

The invention claimed is:
1. A process comprising, in order, the steps of:
(a) providing a first reaction mixture comprising sucrose, a reaction vehicle, and an organotin-based acylation promoter;
(b) removing from the first reaction mixture water produced by reaction between sucrose and the organotin-based acylation promoter to afford a second reaction mixture; and
(c) adding a carboxylic acid anhydride to the second reaction mixture to afford a third reaction mixture, thereby producing a sucrose-6-ester;
in which:
during step (b), the removing of the water includes distillation of the water with the reaction vehicle using an apparatus supplying a heat flux of from 1577 to 78865 W/m² (500 to 25,000 BTU/hrft²) selected from the group consisting of wiped film evaporators, agitated thin film evaporators, falling film evaporators and rising film evaporators, and the reaction vehicle is a polar aprotic solvent;

wherein a non-polar co-solvent is not added during step (b), and wherein the first reaction mixture and/or the second reaction mixture consist essentially of sucrose, polar aprotic solvent, the organotin-based acylation promoter, and/or their reaction products.

2. The process of claim 1, wherein the polar aprotic solvent is N,N-dimethyl formamide.

3. The process of claim 1, wherein the temperature does not exceed about 100° C. in step (b).

4. The process of claim 3, wherein the temperature does not exceed about 80° C. in step (b).

5. The process of claim 4, wherein the temperature does not exceed about 70° C. in step (b).

6. The process of claim 4, wherein the temperature in step (b) is from about 50° C. to about 75° C.

7. The process of claim 1, wherein during step (c) the temperature is maintained at 10° C. or less for a period of time sufficient to produce the sucrose-6-ester.

8. The process of claim 1, wherein the organotin-based acylation promoter is a 1,3-di(acyloxy)-1,1,3,3-tetra-(hydrocarbyl)distannoxane.

9. The process of claim 8, wherein the organotin-based acylation promoter is 1,3-diacetoxy-1,1,3,3-tetrabutyldistannoxane.

10. The process of claim 1, wherein the organotin-based acylation promoter is a 1-(acyloxy)-3-hydroxy-1,1,3,3-tetra-(hydrocarbyl)distannoxane.

11. The process of claim 10, wherein the organotin-based acylation promoter is 1-acetoxy-3-hydroxy-1,1,3,3-tetrabutyldistannoxane.

12. The process claim 1, wherein the carboxylic acid anhydride is acetic anhydride and the sucrose-6-ester is sucrose-6-acetate.

13. The process of claim 1, wherein the carboxylic acid anhydride is benzoic anhydride and the sucrose-6-ester is sucrose-6-benzoate.

14. The process of claim 1, wherein the apparatus supplies a heat flux of from 3155 to 63092 $W/m^2$ (1000 to 20000 $BTU/hrft^2$).

15. The process of claim 14, wherein the apparatus supplies a heat flux of from 15773 to 37855 $W/m^2$ (5000 to 12000 $BTU/hrft^2$).

16. The process of claim 1, wherein the apparatus is a film-type evaporator.

17. The process of claim 1, wherein the apparatus is an agitated thin film evaporator or a wiped film evaporator.

18. The process of claim 1, wherein the distillation is conducted under reduced pressure.

19. The process of claim 18, wherein the pressure is from 2.7 to 5.3 kPa (20 to 40 mmHg).

20. The process of claim 1, wherein the flow rate in the distillation is from 49 to 732 $kg/hr/m^2$ (10 to 150 $lb/hr/ft^2$).

21. The process of claim 20, wherein the flow rate in the distillation is from 244 to 537 $kg/hr/m^2$ (50 to 110 $lb/hr/ft^2$).

22. The process claim 1, additionally comprising, after step (c), the additional step or steps of converting the sucrose-6-ester to sucralose.

* * * * *

UNITED STATES PATENT AND TRADEMARK OFFICE
CERTIFICATE OF CORRECTION

PATENT NO. : 9,073,959 B2  Page 1 of 1
APPLICATION NO. : 12/901820
DATED : July 7, 2015
INVENTOR(S) : Edward Micinski et al.

It is certified that error appears in the above-identified patent and that said Letters Patent is hereby corrected as shown below:

Claims

At Column 20, line 4, Claim 12, "process claim 1" should read -- process of claim 1 --

At Column 20, line 28, Claim 22, "process claim 1" should read -- process of claim 1 --

Signed and Sealed this
First Day of December, 2015

Michelle K. Lee
*Director of the United States Patent and Trademark Office*